United States Patent [19]

Taylor et al.

[11] 4,116,547
[45] Sep. 26, 1978

[54] TACHISTOSCOPIC FOCUS CONTROL

[75] Inventors: Stanford Earl Taylor, Lloyd Harbor; John N. Brucat, Floral Park, both of N.Y.

[73] Assignee: Instructional/Communications Technology, Inc., Huntington Station, N.Y.

[21] Appl. No.: 764,062

[22] Filed: Jan. 31, 1977

[51] Int. Cl.$^2$ .......................... A61B 3/02; G02B 15/00
[52] U.S. Cl. ........................................ 351/31; 350/187
[58] Field of Search ........................... 351/31; 35/35 B; 350/255, 187; 354/195; 353/101

[56] References Cited

U.S. PATENT DOCUMENTS

| | | | |
|---|---|---|---|
| 2,501,219 | 3/1950 | Hopkins et al. | 354/195 X |
| 2,723,591 | 11/1955 | Taylor | 351/31 |
| 3,093,029 | 6/1973 | Johannsen et al. | 353/101 X |
| 3,906,529 | 9/1975 | Filipovich | 350/187 X |

Primary Examiner—Paul A. Sacher
Assistant Examiner—Rodney B. Bovernick
Attorney, Agent, or Firm—Kane, Dalsimer, Kane, Sullivan & Kurucz

[57] ABSTRACT

Apparatus for the tachistoscopic projection of an image of projectable material. The apparatus includes a supporting structure and a light source. A lens mechanism is on the supporting structure optically aligned with the light source. The supporting structure is adapted to support the projectable material between the light source and the lens structure. The apparatus is designed for effecting relative displacement of the lens structure and the support holding the projectable material so as to bring the projected image into focus for a controlled viewing time and then out of focus while the material to be projected is retained stationary in projection position. A cam arrangement is employed which includes a cam surface and a cam follower. A manual actuator is on the lens structure to rotate the lens structure for relative movement between the cam follower and the cam surface and to bring the projected image into and out of focus. The manual actuator is a handle removably attached to the lens structure and manually rotatable to a first position and releasable to rotate to a second position so as to bring the projected image into and out of focus. Finally, the rotational movement between the cam surface and the cam follower causes the one mounted on the lens structure to axially shift the lens structure and accomplish the focusing action for the projected image.

24 Claims, 9 Drawing Figures

FIG. 2
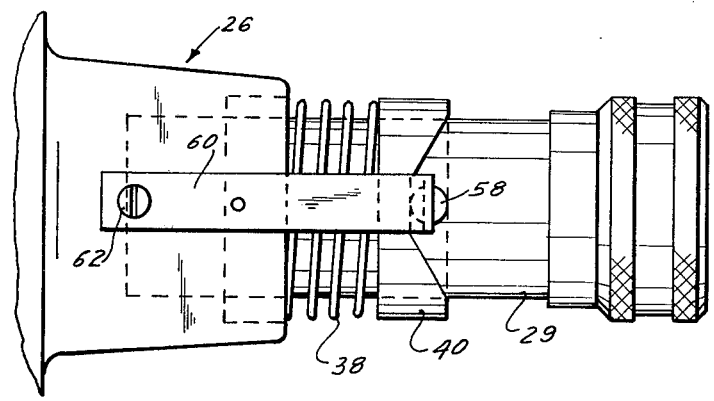
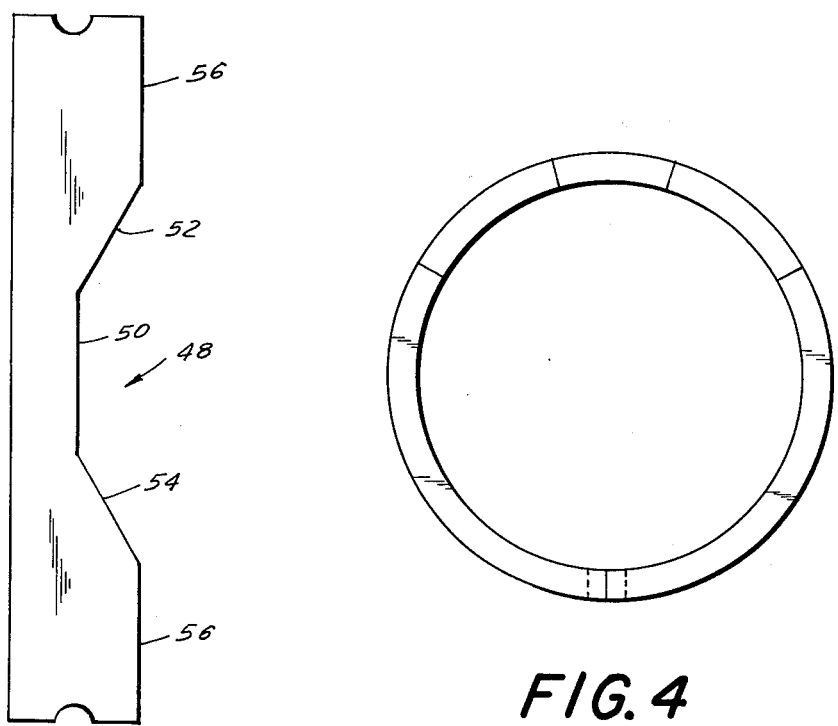
FIG. 4
FIG. 3

TACHISTOSCOPIC FOCUS CONTROL

BACKGROUND OF THE INVENTION

There has been various different types of apparatus and machinery for the tachistoscopic projection of images from film strips and film material in general for assistance as a teaching aid in increasing the ability of a person to visually perceive with greater speed and accuracy and with a greater degree of visual apprehension. Structure of this type is disclosed in U.S. Pat. No. 2,723,591 relating to a Timed Focus Tachistoscope.

Naturally further improvement is always desirable and is particularly advantageous if costs can be materially reduced while obtaining the same and even improved results. Furthermore, it is also advantageous if a device can be developed which is adapted to be attached to conventional projectors, and obtain the same beneficial results.

SUMMARY OF THE INVENTION

With the above background in mind, it is among the primary objectives of the present invention to provide an improved device of the type set forth which is adapted to be mounted on a projector and adjusted so that manual actuation will bring a projected image into and out of focus for a predetermined length of time thus achieving the desirable effects of tachistoscopic projection. The objectives include the development of a device which can be easily attached and adjusted in attachment on a conventional type of projector or viewer and which will operate automatically after manual actuation to shift the lens into and out of focus. The structure is designed so that rotational movement can be manually initiated whereupon gravity will complete rotation of one portion of a cam means which cooperates with a second portion of the cam means to shift the lens into and out of focus position in a timed sequence depending upon the length and configuration of a cam surface as a cam follower follows the cam surface. The speed of movement throughout the travel path, if desired, can be manually controlled and altered by the operator.

Alternatively, the cam means is spring driven in rotational movement. The spring is prebiased by simple manual movement to the start position. The speed of rotation, hence the period of in-focus time, can be controlled by providing the ability to vary the spring load. Naturally, manual control by the operator can also be used to control the speed throughout the travel path.

Various designs for the cam surface are contemplated and the use of a spring assist to facilitate positive focusing action in accordance with the predetermined cam surface configuration is provided. The actuation mechanism is in the form of a weighted handle which will quickly and accurately fall by the force of gravity when actuated to achieve the desired tachistoscopic action with respect to the projected image.

It is an objective to provide a device of the above type which is adapted to be mounted on existing projectors or to be manufactured as part of a new projecting apparatus.

In summary, an apparatus for tachistoscopically projecting an image from projectable material is provided. The apparatus includes a supporting structure, a light source, and lens means on the supporting structure optically aligned with the light source. Means is on the supporting structure for supporting the projectable material between the light source and the lens means. Means is provided for effecting relative displacement of said lens means and said means for supporting material to be projected to bring the projected image into focus for a controlled time and then out of focus while said material to be projected is retained stationary in projection position. The means for effecting relative displacement includes cam means. The cam means includes a cam surface and a cam follower. Manual actuator means is provided to produce relative movement between the cam follower and the cam surface and to bring the projected image into and out of focus. The manual actuator means is in the form of a handle removably attached to the lens means and normally rotatable to a first position and releasable to rotate to a second position. The relative movement between the cam surface and the cam follower causes displacement of the lens means to bring the projected image into and out of focus.

With the above objectives among others in mind, reference is made to the attached drawings.

BRIEF DESCRIPTION OF THE DRAWINGS

In the drawings:

FIG. 2 is a fragmentary top plan view thereof;

FIG. 3 is a plan view of the collar of the apparatus containing the cam surface cut and unrolled into the flat position;

FIG. 4 is an end plan view of the collar portion of the apparatus containing the cam surface;

DESCRIPTION OF THE PREFERRED EMBODIMENTS

Figure 1:
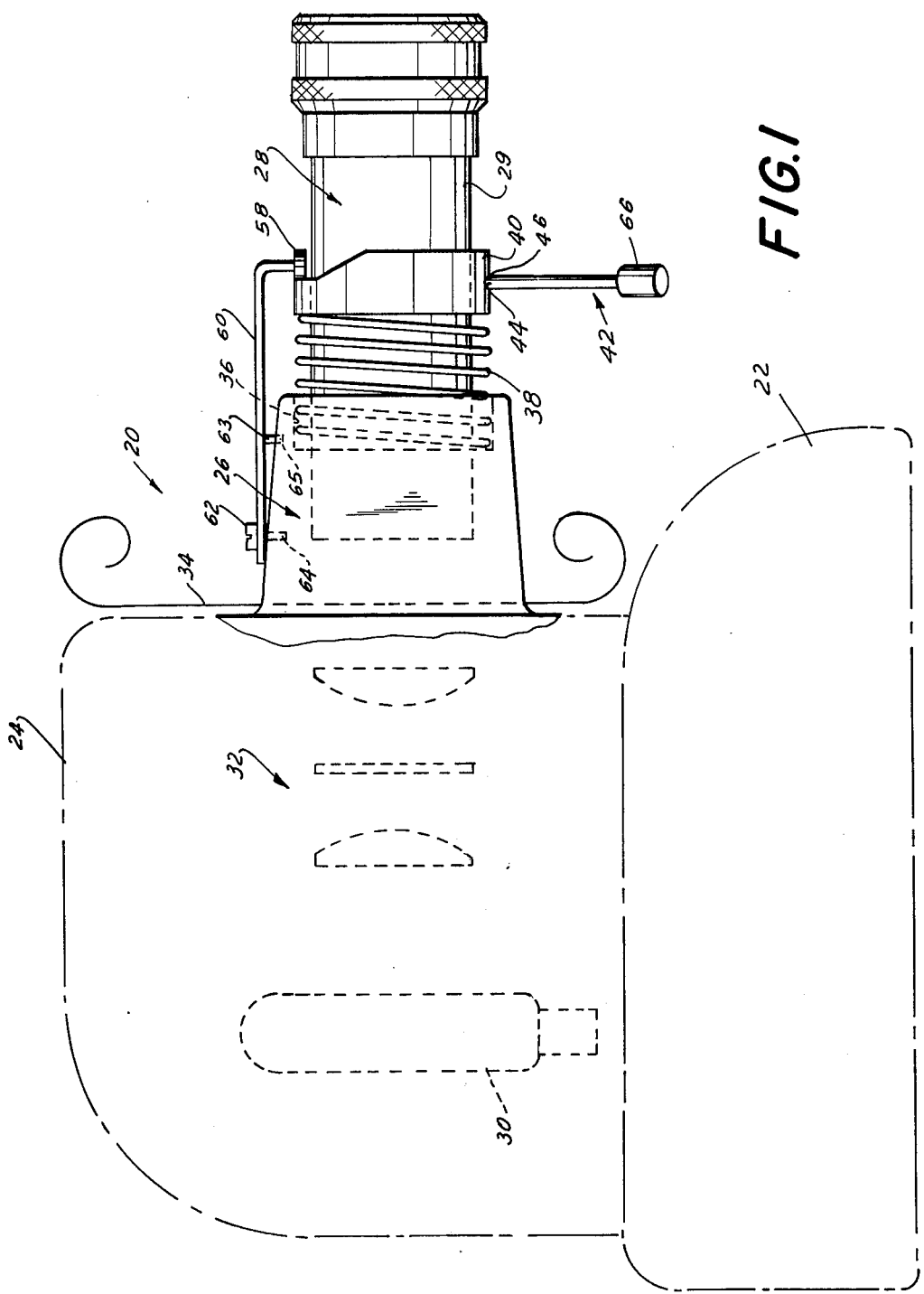
FIG. 1 is a partially sectional side elevation view of an apparatus embodying the invention.

Projector 20 includes a base portion 22 and upper housing portion 24 from which extends a lens holding portion 26 in which is mounted in rotational and slidable relationship in a conventional manner a lens assembly 28. Within upper housing 24 is a projection lamp or light 30 in alignment with a condensing lens arrangement 32. In alignment therewith is projection portion 26 of the housing through which is passed and held a film strip 34 from which the image is to be projected. The film strip is movably vertical from top to bottom in a conventional manner. The lens projection tube or assembly 28 containing the usual projection lens system is mounted for axial reciprocation in portion 26 of the housing. That is, the tube 28 is mounted for movement in reciprocal directions whereby the objective of the projection lens system may be brought into such position that the projected image is focused clearly on the projection screen and moved out of such position at which time the projected image is unrecognizable upon the screen.

The axially slidable lens assembly 28 is mounted in a receiving recess in projection 26 of housing portion 24 of the projector. A recess 36 is positioned adjacent the open end of projector portion 26 and is annular in configuration and larger than the outer diameter of sliding lens assembly 28. Recess 36 captures one end of a helical spring 38. The helical spring 38 surrounds the central portion of the barrel 29 of sliding assembly 28 and has its other end bearing against a circular collar 40 which is mounted on the exterior surface of barrel 29 by conventional means such as a set screw. In the embodiment depicted the set screw is formed by a threaded end portion on handle 42. The threaded end 44 of the handle passes through a threaded aperture 46 in the collar and engages with the outer surface of barrel 29 so as to cooperate with the cam follower in fixing the collar 40 in position on the sliding barrel so that it may slide and rotate therewith. Fixing the threaded end 44 of the handle 42 on the barrel also establishes the angular relationship between the cam follower and the interconnected collar and lens barrel. Collar 40 is generally cylindrical in configuration and has a cam surface 48 cut-out of a portion of the circumference of the collar on the side distal from spring 38. As shown in FIG. 3, this cut-out cam surface 48 has a deeper central portion 50 and two tapered end portions 52 and 54 which extend from communication with central portion 50 to the exterior edge portions 56 of collar 40. When the collar is mounted as shown in FIG. 1, the cam surface 48 is in position for communication with a cam follower pin 58 which extends from a cam follower arm 60. The other end of the cam follower arm 60 is mounted to fixed supporting structure projection 26 by a conventional means such as threaded screw 62 interengaged with a threaded aperture 64 in projection 26. The cam follower pin 58 of arm 60 extends downwardly from the end thereof and into engagement with the cut-out cam surface 50. The cam surface is urged into tighter interengagement with the cam follower pin by the bias from spring 38 which is partially compressed when the collar 40 is mounted to lens barrel 29. To prevent pivoting of arm 60 about screw 62, a second pin 63 extends downwardly from the underside of arm 60 into a receiving aperture 65 in the projection 26.

The end portion of handle 42 distal from collar 40 contains a weight 66 mounted thereon. The weight can be permanently formed as part of a handle or can be slidably and detachably mounted thereon by means of an appropriate set screw or similar fastening device.

As stated above, lens assembly 28 is rotatably and slidably mounted with respect to the fixed projector housing 26 for focusing purposes. The cut-out cam surface 50 has a configuration so that when central portion 50 is in engagement with the cam follower, the projected image from film strip 34 through barrel 29 onto a screen is in focus. In turn, when the cam follower is in engagement with either end portion 52 or 54 of the cut-out the lens barrel will have then axially shifted with respect to the fixed projector housing and, accordingly, the projected image will be out of focus.

In operation, the cam follower surface 48 is positioned with respect to handle 42 so that when the handle is raised to the upper position in engagement with fixed cam arm 60, the follower pin 58 will be positioned adjacent the end portion 56 of cam 48 and the image will be out of focus. Thereafter, when the handle is released and started downwardly, tachistoscopic operation is initiated. The weighted arm will fall under gravitational forces downward through an intermediate position as depicted in FIG. 1 to a final position where it is hanging downwardly. During this automatic travel sequence under the force of gravity the cam follower will pass from an out of focus position along the surface 54 through an in focus position in alignment with surface 50 and then into and out of focus position in alignment with tapered surface 52. Therefore, while the follower pin 58 is in alignment with surface 50 the lens barrel will be in focused position and a focused image will be projected upon the screen. Thus, for a brief period of time during the downward travel sequence of the arm the observer will see a focused image. In contrast at the beginning of the downward stroke and at the end portion of the downward stroke the observer will see a blurred out of focus image.

Thus, tachistoscopic exposure of a film strip or equivalent projectable material is produced by causing the projected image on the screen to be blurred or unreadable, allowing the image to clear or become readable for a predetermined time, and then causing the image to return to an unrecognizable blurred state. This is accomplished automatically during the downward travel of the handle and rotation of the collar attached to barrel 29. The time that the image is distinguishable is determined by the speed of downward travel and the length of cam surface portion 50.

It should also be noted that the handle can be grasped thereafter and rotated upward by hand to the focused position to show the clear image should it be desired. This is helpful in teaching procedures where first the reader is urged to observe the projected image during the brief period of exposure and then he can be shown the exposed image after the sequence for reinforcement or correction. The speed of downward movement of the force of gravity can also be varied by manual control on the part of the operator. He can grasp the handle and speed up or slow down the travel speed at will.

In preparation for the next tachistoscopic exposure, the handle is merely rotated back to the upper or start position and the film strip is advanced to align the next frame with the projection system. The handle 42 is then released and the procedure is repeated.

Figure 5:
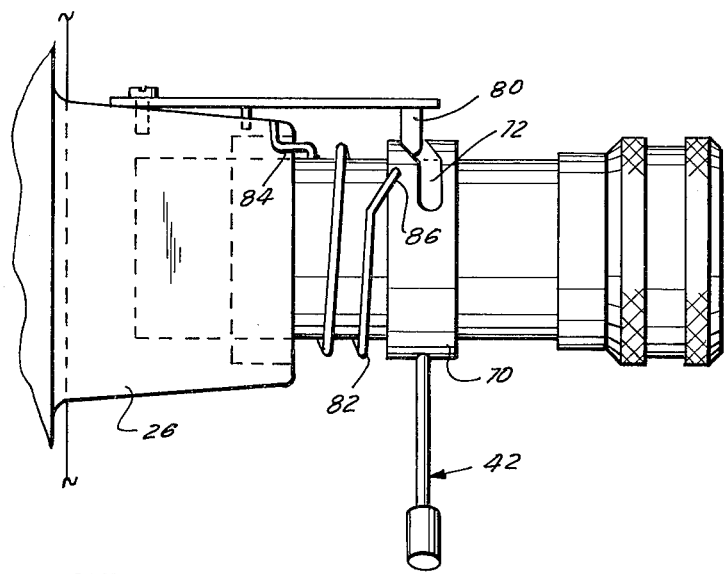
FIG. 5 is a fragmentary top view of an alternative form of the apparatus.
Figure 6:
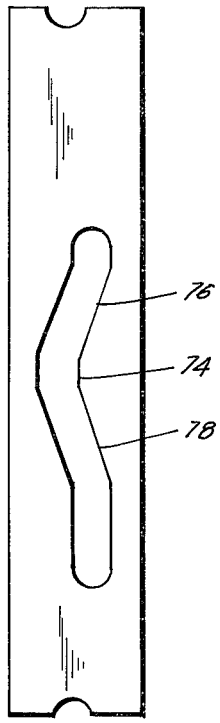
FIG. 6 is an enlarged plan view of the collar portion of the alternative embodiment containing the cam surface cut and unrolled into the flat position.
Figure 7:
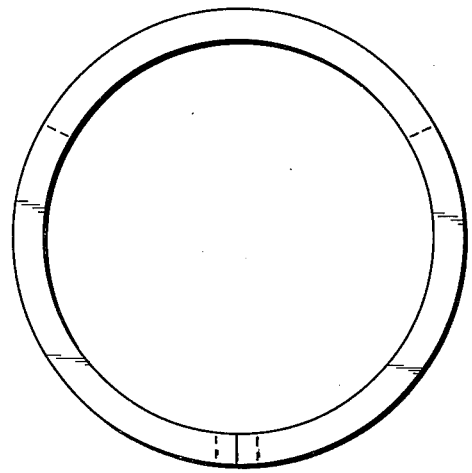
FIG. 7 is an enlarged end plan view of the collar portion of the alternative embodiment.

An alternative embodiment for the collar portion of the apparatus is depicted in FIGS. 5–7 where collar 70 is shown with a cut-out 72 intermediate its forward and rear edges to form the cam surface. Once again, a central focus position 74 is surrounded by two opposing adjacent out of focus positions 76 and 78. In all other respects, with the exception of spring 38 which is not needed since the follower pin 80 is captured in cut-out 72, collar 70 operates in the same manner as collar 40 and cooperates with the remaining structure discussed above in the same manner with cam follower 80 operating like cam follower 58 in controlling the focusing of the lens barrel 29.

One other modification is depicted in the embodiment of FIGS. 5–7 and is the provisions of a helical spring 82. One end 84 of spring 82 is mounted to the projector housing 26 and the other end 86 of spring 82 is mounted to rotatable collar 70. Thus, when the collar is appropriately rotated, spring 82 will be biased and a load applied to the spring. Accordingly, when the collar is then released, the prebiased spring will unwind and drive the collar rotationally and correspondingly shift the cam slot with respect to the cam follower so as to bring the image into and out of focus in the manner described above. This system is in contrast to merely relying upon gravitational force to rotate the collar. Naturally, the force supplied by the spring can be varied by employing different springs or different anchor points for different desired forces. In all other respects, operation of the system remains the same as in the previously discussed embodiments with handle 42 merely rotated to the start position and than released.

Figure 8:
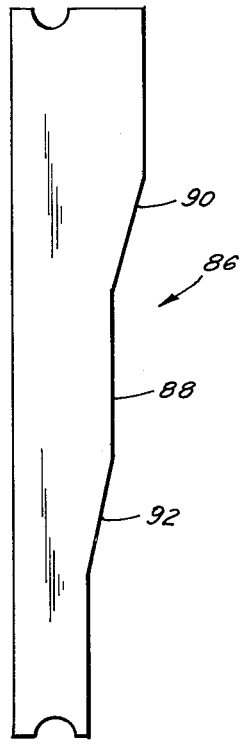
FIG. 8 is an enlarged plan view of the collar portion of a further alternative embodiment containing the cam surface cut and unrolled into the flat position.
Figure 9:
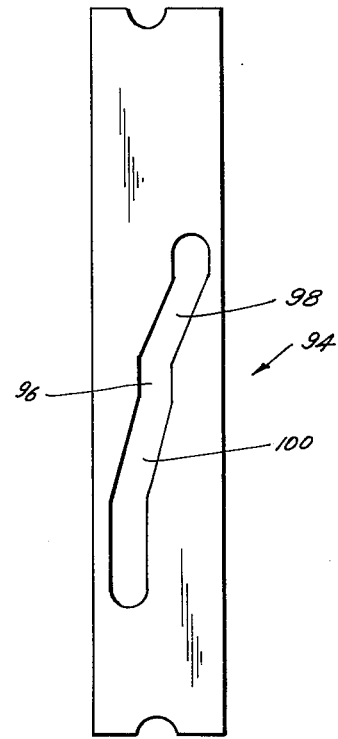
FIG. 9 is an enlarged plan view of the collar portion of a still further alternative embodiment containing the cam surface cut and unrolled into the flat position.

While two different configurations are depicted in FIGS. 1-7 of the drawings for the cam surface in collars 40 and 70, it can be readily envisioned how a great variety of different cam surfaces can be employed as long as there is a focus portion and at least one out of focus portion. FIGS. 8 and 9 depict two alternative cam surfaces which could be readily employed with the embodiments described above. In FIG. 8, the collar 86 has a central in focus portion 88, an outwardly tapering out of focus portion 90 at one end and an inwardly tapering out of focus portion 92 at the other end. Collar 86 is adapted to be used with the embodiment of FIGS. 1-4 without modification of the remaining components of the apparatus. As collar 86 rotates, the cam follower passes through out of focus portion 90, into in focus portion 88 and then into out of focus portion 92. In FIG. 9, the collar 94 has an irregularly shaped slot between its edges including a central in focus portion 96, and outwardly tapering out of focus portion 98 at one end and an inwardly tapering out of focus portion 100 at the other end. Collar 94 is adapted to be used with the embodiment of FIGS. 1-4 without modification of the remaining components of the apparatus. As collar 94 rotates, the cam follower passes through out of focus portion 98, into in focus portion 96 and then into out of focus portion 100.

It is also possible that the cam surface could be formed on arm 60 and the cam follower located on the collar. Also, the cam surface could be formed directly on the lens barrel. The apparatus would operate in the same manner in all other respects with only the location of the cam follower and cam surface being reversed with respect to the movable and fixed parts.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. Apparatus for the tachistoscopic projection of an image from projectable material comprising:
 a supporting structure;
 a light source;
 lens means on the supporting structure optically aligned with the light source;
 means on the supporting structure for supporting the projectable material between the light source and the lens means;
 cam means including a cam surface and a cam follower to effect relative displacement of said lens with respect to the stationary supported material to be projected to bring the projected image from an out of focus condition to an in focus condition for a rapid controlled time period and then to an out of focus condition again; manual actuator means to produce relative movement between the cam follower and the cam surface thereby bringing the projected image from a first out of focus condition into a controlled rapid focus condition and then into an out of focus condition again; the manual actuator being a handle and being normally rotatable to a first position and releasable to rotate to a second position.

2. The invention in accordance with claim 1 wherein the handle is normally rotatable to an upper position and releasable to fall by gravity to a lower position.

3. The invention in accordance with claim 2 wherein the handle is an elongated tubular member having a weight on its free end thereby facilitating the gravitational fall of the handle and consequent shifting of the lens into and out of focus.

4. The invention in accordance with claim 2 wherein the handle is attached by means of a threaded end which is interengaged with a threaded aperture in the supporting structure.

5. The invention in accordance with claim 1 wherein the cam surface is attached to the lens means and the cam follower is on a fixed portion of the supporting structure.

6. The invention in accordance with claim 5 wherein the cam surface is formed as an irregularly shaped cutout on a tubular collar adapted to be surroundingly coupled to the lens means in fixed position thereon.

7. The invention in accordance with claim 6 wherein the cam surface is an irregular recess formed in one edge portion of the collar for a predetermined portion of the circumference of the collar.

8. The invention in accordance with claim 7 wherein a helical spring is captured between the collar and the adjacent supporting structure and tends to bias the collar and displaceable structure axially away from the adjacent supporting structure so as to retain the collar in position for engagement between the cam recess therein and the cam follower mounted on the supporting structure so that as the cam follower follows the cam recess axial movement of the collar and lens will be facilitated by the bias supplied by the spring, to hold the cam follower in tight engagement with the surface of the collar forming the recess and the lens being focused by movement of the displaceable structure with respect to the supporting structure.

9. The invention in accordance with claim 6 wherein the cam surface is an irregular slot formed along a predetermined portion of the surface of the tubular collar and located intermediate the edges thereof.

10. The invention in accordance with claim 1 wherein the manual actuator means includes a spring, one end of the spring attached to the surfaces containing the cam follower and the other end of the spring mounted to the surfaces containing the cam surface whereby rotation of the handle to the first position will bias the spring so that release of the handle will permit the handle to be rotated to the second position with the assistance of force exerted by the biased spring.

11. The invention in accordance with claim 6 wherein the cam follower is in the form of an elongated arm terminating in a downwardly extending pin adjacent one end, the pin being adapted to project within the cam surface in the collar, the arm being mounted in fixed position on the supporting structure so that rotation of the collar will cause its axial movement with respect to the pin and correspondingly bring the lens means into and out of focus.

12. The invention in accordance with claim 11 wherein the arm of the cam follower is mounted to the supporting structure by means of a threaded screw passed through the end portion of the arm distal from the pin and into a threaded aperture in the supporting structure and a second pin spaced from the first pin and intermediate the ends of the arm and extending into an aligned receiving aperture in the supporting structure.

13. A device adapted to be attached to an apparatus for projecting an image from projectable material to permit tachistoscopic projection of the image in a manner which increases the ability to visually perceive with greater speed, accuracy and apprehension the projected material, the apparatus including a supporting structure, a light source, lens means on a displaceable portion of the supporting structure and being optically aligned with the light source, means for supporting the projectable material between the light source and the lens means in stationary position, the device comprising; cam means including a cam surface and a cam follower with one of the surface and follower adapted to be mounted on the supporting structure and the other of the surface and follower adapted to be mounted on the displaceable portion whereby relative movement between the surface and follower will shift the lens means to bring the projected image from the stationary projectable material from an initial out of focus condition into a rapid controlled in focus condition and then to a further out of focus condition, manual actuated means on the cam means to rotate the displaceable portion when the device is attached thereto for movement of the cam follower with respect to the cam surface to shift the projected image from the initial out of focus condition, through the controlled in focus condition and then again into an out of focus condition, the manual actuator being a handle removably attached to the cam means and normally rotatable to a first position and releasable to rotate to a second position so as to produce the desired focusing of the projected image.

14. The invention in accordance with claim 13 wherein the handle is normally rotatable to an upper portion and releasable to fall by gravity to a lower position.

15. The invention in accordance with claim 14 wherein the handle is an elongated tubular member having a weight on the end distal from the handle attached to the displaceable portion thereby facilitating the gravitational fall of the handle and consequent focusing action.

16. The invention in accordance with claim 13 wherein the handle is attached to the displaceable portion by means of a threaded end which is interengaged with a threaded aperture in the displaceable portion.

17. The invention in accordance with claim 13 wherein the cam surface is on the displaceable portion and the cam follower is on the supporting structure.

18. The invention in accordance with claim 13 wherein the cam surface is formed as an irregularly shaped cut-out on a tubular collar adapted to be surroundingly coupled to the displaceable portion in fixed position.

19. The invention in accordance with claim 18 wherein the cam surface is an irregular recess formed in one edge portion of the collar for a predetermined portion of the circumference of the collar.

20. The invention in accordance with claim 19 wherein a helical spring is captured between the collar and the adjacent supporting structure and tends to bias the collar and displaceable portion axially away from the adjacent supporting structure so as to retain the collar in position for engagement between the cam recess therein and the cam follower mounted on the supporting structure so that as the cam follower follows the cam recess axial movement of the collar and displaceable portion will be facilitated by the bias supplied by the spring, to hold the cam follower in tight engagement with the surface of the collar forming the recess and the lens means being focused by movement of the displaceable portion with respect to the supporting structure.

21. The invention in accordance with claim 18 wherein the cam surface is an irregular slot formed along a predetermined portion of the surface of the tubular collar and located intermediate the edges thereof.

22. The invention in accordance with claim 13 wherein the manual actuator means includes a spring, one end of the spring attached to the surfaces containing the cam follower and the other end of the spring mounted to the surfaces containing the cam surface whereby rotation of the handle to the first position will bias the spring so that release of the handle will permit the handle to be rotated to the second position with the assistance of force exerted by the biased spring.

23. The invention in accordance with claim 13 wherein the cam follower is in the form of an elongated arm terminating in a downwardly extending pin adjacent one end, the pin being adapted to project within the cam surface in a collar, the arm being mounted in fixed position on the supporting structure so that rotation of the collar will cause its axial movement with respect to the pin and correspondingly bring the lens means into and out of focus.

24. The invention in accordance with claim 23 wherein the arm of the cam follower is mounted to the supporting structure by means of a threaded screw passed through the end portion of the arm distal from the pin and into a threaded aperture in the supporting structure and a second pin spaced from the first pin and intermediate the ends of the arm and extending into an aligned receiving aperture in the supporting structure.

* * * * *